United States Patent [19]
Oshida et al.

[11] Patent Number: 6,046,201
[45] Date of Patent: *Apr. 4, 2000

[54] PYRIDINECARBOXAMIDE DERIVATIVES

[75] Inventors: Norio Oshida; Yoji Mimaki; Hiroaki Satoh, all of Saitama-ken; Shinji Yokoyama, Komoro; Yukiko Muraki, Saitama-ken; Kazumi Nishimura, Saitama-ken; Tamiko Hamada, Saitama-ken; Einosuke Sakurai, Saitama-ken; Hiroshi Sakai, Saitama-ken; Toshiji Sugai, Saitama-ken; Tomomi Tonoike, Saitama-ken; Koichi Itoh, Saitama-ken, all of Japan

[73] Assignee: Nisshin Flour Milling Co., Ltd., Tokyo, Japan

[*] Notice: This patent is subject to a terminal disclaimer.

[21] Appl. No.: 09/101,441

[22] PCT Filed: Nov. 19, 1997

[86] PCT No.: PCT/JP97/04208

§ 371 Date: Jul. 15, 1998

§ 102(e) Date: Jul. 15, 1998

[87] PCT Pub. No.: WO98/22440

PCT Pub. Date: May 28, 1998

[30] Foreign Application Priority Data

Nov. 19, 1996 [JP] Japan ................................. 8-308509

[51] Int. Cl.⁷ ...................... A61K 31/495; C07D 401/04
[52] U.S. Cl. ............................................ 514/252; 544/365
[58] Field of Search .............................. 544/365; 514/252

[56] References Cited

U.S. PATENT DOCUMENTS

| | | | |
|---|---|---|---|
| 4,994,456 | 2/1991 | Miura et al. | 514/218 |
| 5,025,012 | 6/1991 | Miura et al. | 514/252 |
| 5,250,526 | 10/1993 | Miura et al. | 514/218 |

FOREIGN PATENT DOCUMENTS

| | | |
|---|---|---|
| 3-7258 | 1/1991 | Japan . |
| 3-137095 | 6/1991 | Japan . |
| 5-32630 | 2/1993 | Japan . |

OTHER PUBLICATIONS

Otomo et al., "Clinical Efficacy of a Free Radical Scavenger, MCI–186 on Acute Cerebral Infarction," Therapeutic Research, vol., 19, No. 4, pp. 551–552, 1998.

Dorman et al., "Recently Developed Neuroprotective Therapies for Acute Stroke," CNS Drugs, vol. 6, pp. 457–474, Jun. 1996.

Stroke, A Journal of Cerebral Circulation, vol. 12, No. 6, Nov.–Dec. 1981 J. Astrup et al,.

K. Inamura et al. Brain Nerve, 44(9): 779–785, 1992.

T. Asano et al., Neurosurgery, 13 (11): 1147–1159, 1985.

T. Kirino, Brian Research, 239: 57–69, 1982.

A. Ogura et al., Exptl. Brain Res., 73:447–458, 1988.

E. Sakurai et al., Jpn. J. Pharmacol., vol. 61, No. Suppl. 1, p. 289p 1993.

H. Nishi et al., Stroke, 20: 1236–1240, 1989.

*Primary Examiner*—Mukund J. Shah
*Assistant Examiner*—Ann M. Kessinger
*Attorney, Agent, or Firm*—Oblon, Spivak, McClelland, Maier & Neustadt, P.C.

[57] ABSTRACT

N-(12-Nitroxydodecyl)-6-(4-ethyl or isopropyl-1-piperazinyl)pyridine-3-carboxamide or physiologically acceptable salts thereof. The said compounds have excellent inhibiting activity of cerebral edema, especially ischemic cerebral edema, and inhibiting activity of delayed neuronal death (an inhibiting activity of Ca-influx in neuronal cells). Cerebral edema is a pathologic condition accompanying cerebrovascular disorders, especially the acute stage cerebrovascular disorders and then the compounds are useful as an inhibiting agent for cerebral edema or a therapeutic agent for cerebrovascular disorders. Moreover, because the compounds do hardly show a behavior suppressing action, which is considered to be side effect in treating cerebrovascular disorders at the acute stage, they are an excellent therapeutic agent for, in particular, the acute stage cerebrovascular disorders. Moreover, the compounds show a cerebral protective activity (an anti-anoxic activity), an activity of increasing cerebral blood flow, and an activity of inhibiting lipid peroxidation, and these activities may lead to the increased utility as a therapeutic agent for cerebrovascular disorders.

5 Claims, No Drawings

PYRIDINECARBOXAMIDE DERIVATIVES

This application is a 371 of PCT/JP97104208, filed Nov. 19, 1997.

TECHNICAL FIELD

This invention relates to a pyridinecarboxamide derivative. More particularly, this invention relates to an N-(12-nitroxydodecyl)-6-piperazinylpyridine-3-carboxamide derivative, a process for the preparation thereof and a pharmaceutical preparation which comprises as an active ingredient said derivative. Moreover, this invention relates to a therapeutic agent for cerebrovascular disorders or cerebral edema which comprises as an active ingredient said pyridine carboxamide derivative. Moreover, this invention relates to a method for the treatment of cerebrovascular disorders or cerebral edema which comprises administering said pyridinecarboxamide derivative. Moreover, this invention relates to an intermediate for the synthesis of said pyridinecarboxamide derivative.

BACKGROUND ART

Neuronal cells are weak to ischemia and may easily be damaged, but there is a recoverable area around the ischemic neuronal cells, which is referred to as the "Penumbra" (Astrup, J., Siesjo, B., Symon, L.; Stroke, 12:723–725 1981). In the therapy of cerebrovascular disorders at the acute stage, it is important to protect the neuronal cells in the penumbra area from cell damage and maintain cerebral functions.

It has been known that cerebrovascular disorders caused by ischemia may accompany cerebral edema with an unusually increased moisture content in the brain in the ischemic center and penumbra area (Kenji Inamura and Akiro Terashi: Brain Nerv. 44(9): 779–785, 1992). Cerebral edema may be also caused by cerebral tumor, encephalitis, heat stroke, cerebral trauma by a traffic accident. The edema may increase the cerebral capacity, which results in the increase in cerebral pressure, because the brain is closed within the hard skull. A precipitous increase in cerebral pressure may cause cerebral hernia, which makes patients fall in the dangerous state of their life.

Cerebral edema may accompany sodium and calcium influx into neuronal cells, which are found at a higher concentration extracellularly as compared with the intracellular one (Takao Asano, Hiroo Johshita, Osamu Gotoh and others: Cerebral Surgery 13: 1147–1159, 1985), and it is believed that calcium influx may activate calcium-dependent enzymes (proteases, phospholipases or the like), which results in the damage of cytoskeleton or cell membrane.

Activation of phospholipase A2, a phospholipase, may release arachidonic acid from the phospholipid in cell membrane. Accumulation of the arachidonic acid may inhibit respiration of mitochondria to decrease ATP. Moreover, it is believed that peroxidation of lipids by the free radicals produced during the metabolism of arachidonic acid may cause disorders of cell membrane or increased permeability of the membrane to provoke the progress of the edema.

In addition to such acute disorders of neuronal cells, the phenomenon referred to as the delayed neuronal death has been found out (Kirino T., Brain Res., 239: 57–69, 1982). This means the phenomenon that the neuronal cells after a short period of ischemia fall off after several days to several weeks. It has now been elucidated that delayed cellular death such as delayed neuronal death is related with a calcium concentration in neuronal cells (Ogura, A., Miyamoto, M., Kudo, Y., Exptl. Brain Res., 73:447–458, 1988). Such being the case, it is the important object in the treatment of cerebrovascular disorders at the acute stage to inhibit cerebral edema which would greatly influence upon the prognosis for life of patients and also could be the cause of acute and delayed neuronal death.

Presently there has been mainly applied an osmotherapy for the treatment of cerebral edema. In this method, a liquid of hyperosmorality is injected into blood, whereby an osmotic pressure in blood is raised and moisture is withdrawn from edema tissues. However, satisfactory effects have not been attained as yet and there has been desired a novel anti-cerebral edema agent other than the osmotherapy.

On the other hand, our copending JP-A-5-32630 discloses that pyridinecarboxamide derivatives having a methylene chain of 9–13 carbon atoms and bonded to the amido nitrogen have an activity of increasing cerebral blood flow. Moreover, it was reported by Sakurai et al. that the compound of Example 10 of said JP-A-5-32630, namely, N-(11-nitroxy-1-undecanyl)-6-(4-methyl-1-piperazinyl)nicotinamide could show a cerebral protective effect on the hypoxia and anoxia models (Sakurai Einosuke, Jpn. J. Pharmacol., Vol. 61, No. suppl. 1, PAGE 289p 1993).

As the compounds having a cerebral protective action (an anti-anoxia action) would be expected to show an inhibiting action on cerebral edema, it has been attempted to review and pick up those compounds having an anti-anoxia action. However, the compounds disclosed in Example 10 of JP-A-5-32630 have been regarded as undesirable for the therapy of cerebrovascular disorders at the acute stage, because they were observed to possess a behavior suppressing activity that Nizofenone and others possess as a side effect.

DISCLOSURE OF INVENTION

This invention relates to a pyridinecarboxamide derivative represented by the formula (1)

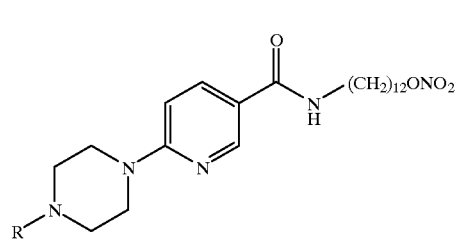

(1)

(wherein R represents an ethyl group or an isopropyl group) or a physiologically acceptable salt thereof.

Moreover, this invention relates to a compound represented by the formula (2)

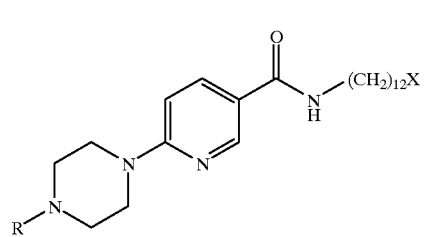

(2)

(wherein R is as defined above and X represents a hydroxyl group, a mesyloxy group, a tosyloxy group, a bromine atom or an iodine atom).

Moreover, this invention relates to a 6-piperazinylpyridine-3-carboxylic acid represented by the formula (3)

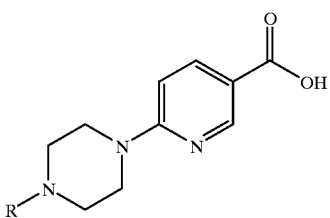

(3)

(wherein R is as defined above) or a metal salt or acid addition salt thereof.

Moreover, this invention relates to a process for the production of the pyridinecarboxamide derivative represented by the formula (1) which comprises reacting the compound represented by the abovementioned formula (2) with a nitrating agent.

Moreover, this invention relates to a process for the production of the pyridinecarboxamide derivative represented by the formula (1) which comprises reacting an alkali metal salt, a halide or an anhydride of the 6-piperazinylpyridine-3-carboxylic acid represented by the formula (3) with a 12-aminoalkyl nitrate represented by the formula (4)

$$H_2N(CH_2)_{12}ONO_2 \quad (4)$$

or an acid addition salt thereof.

Moreover, this invention relates to a pharmaceutical composition for treating cerebrovascular disorders, especially cerebrovascular disorders at the acute stage, which comprises the pyridinecarboxamide derivative represented by the formula (1) or a physiologically acceptable salt thereof and a pharmaceutically acceptable excipient.

Moreover, this invention relates to the therapeutic agent for cerebrovascular disorders at the acute stage which is used for treating cerebrovascular disorders caused by cerebral infarction or subarachnoid hemorrhage.

Moreover, this invention relates to the therapeutic agent for cerebral edema which comprises the pyridinecarboxamide derivative represented by the formula (1) or a physiologically acceptable salt thereof and a pharmaceutically acceptable excipient.

Moreover, this invention relates to a method for the treatment of cerebrovascular disorders, especially cerebrovascular disorders at the acute stage, which comprises administering the pyridinecarboxamide derivative represented by the formula (1) or a physiologically acceptable salt thereof to patients suffering from cerebrovascular disorders, especially cerebrovascular disorders at the acute stage.

Moreover, this invention relates to a method for the treatment of cerebral edema which comprises administering the pyridinecarboxamide derivative represented by the formula (1) or a physiologically acceptable salt thereof to patients suffering from cerebral edema.

The pyridinecarboxamide derivatives (1) of this invention have excellent inhibiting activity of cerebral edema and inhibiting activity of delayed neuronal death (inhibiting activity of Ca-influx in neuronal cells), and further a cerebral protective action (an anti-anoxia action), and an inhibiting action on peroxidation of lipids, while they have no behavior suppressing activity which is believed to be side effects so that they are highly useful as a therapeutic agent for cerebrovascular disorders. The pathologic type of cerebrovascular disorders to which the therapeutic agent for cerebrovascular disorders of the present invention may be applied includes cerebral hemorrhage, brain infarction (cerebral thrombosis, cerebral infarction), transient ischemic attack, subarachnoid hemorrhage and others. The cerebrovascular disorders at the acute stage as stated herein is meant to indicate the cerebrovascular disorders at the period of time of less than one month after the onset of cerebrovascular disorders.

Almost all cerebrovascular disorders at the acute stage are accompanied with cerebral edema which may accelerate microcirculation disorders around lesions to make cerebral disorders far worse.

Delayed neuronal death is meant to indicate the neuronal death wherein neuronal cells such as hippocampus CA fall off several days after a severe transient global cerebral ischemia due to temporal cardiac arrest and others. The mechanism of this action is believed to be an increase in glutamic acid and subsequent increase in intracellular calcium, and thus the pyridinecarboxamide derivatives of this invention, which can inhibit the delayed neuronal death, are useful as a therapeutic agent for cerebrovascular disorders.

Moreover, energy deficiency caused by ischemia or release of neurotransmitters such as glutamine and the like may cause influx of calcium ions into cells and generation of free radicals. Excessive production of free radicals may accelerate the formation of lipoperoxide and may cause irreversible disorders of cell membrane and rise in permeability of membrane, which leads to cerebral edema and neuronal death. Accordingly, the pyridinecarboxamide derivatives of the invention which inhibit the influx of calcium ions and the formation of lipoperoxide are useful as a therapeutic agent for cerebrovascular disorders at the acute stage.

The compounds (2) and compounds (3) of this invention are useful as intermediates for the synthesis of the pyridinecarboxamide derivatives (1).

The pyridinecarboxamide derivatives represented by the formula (1) can be produced by reacting the compounds of the formula (2) with a nitrating agent such as nitric acid, fuming nitric acid, tetrabutylammonium nitrate, strongly basic ion exchange resins (e.g., Amberlyst) of a nitrate form, silver nitrate or potassium nitrate in the presence or absence of a solvent at −40° C. to 120° C., preferably −40° C. to room temperature. As the solvent, there may be mentioned dichloromethane, chloroform, carbon tetrachloride, diethyl ether, tetrahydrofuran, toluene, acetonitrile, acetic anhydride, sulfuric acid, etc. and a mixed solvent thereof.

Moreover, the pyridinecarboxamide derivatives represented by the formula (1) may be also produced by condensing 12-aminododecyl nitrate or a salt thereof with a salt of the compound of the formula (3) or a reactive intermediate thereof.

Specific examples of salts of 12-aminododecyl nitrate may include nitrate, hydrochloride or the like.

Specific examples of the salts or reactive intermediates of the compounds of the formula (3) may include sodium 6-(4-ethyl-1-piperazinyl)pyridine-3-carboxylate, potassium 6-(4-ethyl-1-piperazinyl)pyridine-3-carboxylate, 6-(4-ethyl-1-piperazinyl)pyridine-3-carbonyl chloride, sodium 6-(4-isopropyl-1-piperazinyl)-pyridine-3-carboxylate, potassium 6-(4-isopropyl-1-piperazinyl)pyridine-3-carboxylate, 6-(4-isopropyl-1-piperazinyl)pyridine-3-carbonyl chloride and the like.

The compounds (1) can be preferably produced by reacting a salt of the compound (3) with 0.5 to 4 equivalents of 12-aminododecyl nitrate or a salt thereof in a solvent in the presence of 0.5 to 4 equivalents of a condensing agent at −40° C. to 40° C., preferably 0° C. to room temperature. There may be incorporated in situ 0.5 to 4 equivalents of an additive and a base. As the solvent, there may be mentioned dichloromethane, chloroform, carbon tetrachloride, tetrahydrofuran, diethyl ether, dioxane, benzene, toluene, xylene, acetonitrile, dimethylformamide, dimethyl sulfoxide and the like and a mixed solvent thereof. As the condensing agent, there may be mentioned carbodiimides such as dicyclohexylcarbodiimide, 1-ethyl-3-(3-dimethylaminopropyl)carbodiimide hydrochloride and the like, azides such as diphenylphosphoryl azide and the like, carbonyldiimidazole, diethyl pyrocarbonate and the like. As the additive, there may be mentioned N-hydroxysuccinimide, 1-hydroxybenzotriazole and the like and, as the base, there may be mentioned organic bases such as triethylamine, diisopropylethylamine, pyridine, and the like.

12-Aminododecyl nitrate (4) or a salt thereof can be synthesized from 12-aminododecanol or an active intermediate thereof such as 12-bromododecylamine, 12-iodododecylamine, 12-aminododecyl methanesulfonate, 12-aminododecyl p-toluenesulfonate and the like, in similar conditions to those for the compound (1).

The compounds of the formula (2) wherein X is a bromine atom or an iodine atom can be synthesized by reacting the compounds wherein X is a hydroxyl group with hydrobromic acid or hydriodic acid.

The compounds of the formula (2) wherein X is an iodine atom can be also synthesized by reacting the compounds wherein X is a mesyloxy group or a tosyloxy group with sodium iodide or potassium iodide in acetone.

The compounds of the formula (2) wherein X is a mesyloxy group or a tosyloxy group can be synthesized by reacting the compounds wherein X is a hydroxyl group with mesyl chloride or tosyl chloride in the presence of a base.

The compounds of the formula (2) can be synthesized by reacting a compound of the formula (3) or a reactive intermediate thereof such as a sodium salt or potassium salt or acid halide thereof with a compound of the formula (5)

$$H_2N(CH_2)_{12}X \quad (5)$$

(wherein X is a bromine atom, an iodine atom, a mesyloxy group, a tosyloxy group or a hydroxyl group) in a solvent in the presence of 0.5 to 4 equivalents of a condensing agent at a temperature from −40° C. to 40° C. There may be incorporated in situ 0.5 to 4 equivalents of an additive and a base. As the solvent, there may be mentioned dichloromethane, chloroform, carbon tetrachloride, tetrahydrofuran, diethyl ether, dioxane, benzene, toluene, xylene, acetonitrile, dimethylformamide, dimethyl sulfoxide, and the like and a mixed solvent thereof. As the condensing agent, there may be mentioned carbodiimides such as dicyclohexylcarbodiimide, 1-ethyl-3-(3-dimethylaminopropyl)-carbodiimide hydrochloride, and the like, azides such as diphenylphosphoryl azide, and the like, carbonyldiimidazoles, diethyl pyrocarbonate and the like. As the additive, there may be mentioned N-hydroxysuccinimide, 1-hydroxybenzotriazole and the like and, as the base, there may be mentioned organic bases such as triethylamine, diisopropylethylamine, pyridine and the like.

The compounds of the formula (2) wherein X is a hydroxyl group can be produced by reacting a compound of the formula (6)

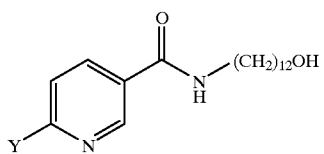

(6)

(wherein Y is a halogen atom such as chlorine, bromine, iodine or the like) with 1 to 100 equivalents of a compound of the formula (7)

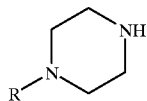

(7)

(wherein R is as defined above) in the presence or absence of a solvent at a temperature from room temperature to a reflux temperature or in a sealed tube. There may be also incorporated 0.05 to 10 equivalents of sodium iodide or potassium iodide in situ, or 0.5 to 10 equivalents of a base may be incorporated. As the solvent, there may be mentioned dichloromethane, chloroform, carbon tetrachloride, tetrahydrofuran, diethyl ether, dioxane, benzene, toluene, xylene, acetonitrile, dimethylformamide, dimethyl sulfoxide, methanol, ethanol, and the like and a mixed solvent thereof. As the base, there may be mentioned inorganic bases such as sodium hydrogen carbonate, sodium carbonate, potassium carbonate, cesium carbonate, and the like or organic bases such as triethylamine, diethylamine, diisopropylamine, diisopropylethylamine, pyridine, and the like The compounds of the formula (2) can be also prepared by reacting a compound of the formula (6) with 1 to 100 equivalents of piperazine in the presence or absence of a solvent at a temperature from room temperature to a reflux temperature or in a sealed tube to form the compound of the formula (8)

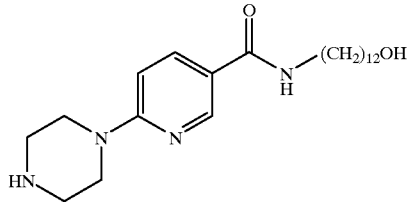

(8)

and then reacting the compound of the formula (8) thus obtained with 1 to 10 equivalents of a compound of the formula RZ [wherein R is as defined above and Z represents a halogen atom such as chlorine, bromine, iodine and the like or a leaving group such as a sulfonate (e.g., a methanesulfonyloxy group, a toluenesulfonyloxy group) in the presence or absence of a solvent at a temperature from room temperature to a reflux temperature or in a sealed tube. There may be also incorporated 0.05 to 4 equivalents of sodium iodide or potassium iodide in situ, or 0.5 to 10 equivalents of a base may be incorporated. As the solvent, there may be mentioned dichloromethane, chloroform, carbon tetrachloride, tetrahydrofuran, diethyl ether, dioxane, benzene, toluene, xylene, acetonitrile, dimethylformamide, dimethyl sulfoxide, methanol, ethanol, and the like and a mixed solvent thereof. As the base, there may be mentioned inorganic bases such as sodium hydrogen carbonate, sodium carbonate, potassium carbonate, cesium carbonate, and the like or organic bases such as triethylamine, diethylamine, diisopropylamine, diisopropylethylamine, pyridine, and the like.

The compounds of the formula (6) can be prepared by reacting a compound of the formula (9)

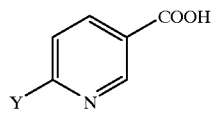
(9)

(wherein Y is as defined above) with 0.5 to 4 equivalents of the compound of the formula (10)

H$_2$N(CH$_2$)$_{12}$OH (10)

in a solvent in the presence of 0.5 to 4 equivalents of a condensing agent at a temperature from −40° C. to 40° C. There may be incorporated in situ 0.5 to 4 equivalents of an additive and a base. As the solvent, there may be mentioned dichloromethane, chloroform, carbon tetrachloride, tetrahydrofuran, diethyl ether, dioxane, benzene, toluene, xylene, acetonitrile, dimethylformamide, dimethyl sulfoxide, and the like and a mixed solvent thereof. As the condensing agent, there may be mentioned carbodiimides such as dicyclohexylcarbodiimide, 1-ethyl-3-(3-dimethylaminopropyl)carbodiimide hydrochloride and the like, azides such as diphenylphosphoryl azide, and the like, carbonyldiimidazole, diethyl pyrocarbonate and the like. As the additive, there may be mentioned N-hydroxysuccinimide, 1-hydroxybenzotriazole and the like and, as the base, there may be mentioned organic bases such as triethylamine, diisopropylethylamine, pyridine and the like.

The compounds of the formula (3) can be also prepared by reacting a compound of the formula (11)

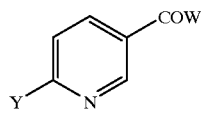
(11)

(wherein Y is as defined above and W represents a halogen atom such as chlorine, bromine, iodine, and the like) with 0.5 to 4 equivalents of the compound of the formula (10) in a solvent at a temperature from −40° C. to 40° C. There may be incorporated in situ 0.5 to 4 equivalents of a base. As the solvent, there may be mentioned dichloromethane, chloroform, carbon tetrachloride, tetrahydrofuran, ether, dioxane, benzene, acetonitrile, dimethylformamide, dimethyl sulfoxide, and the like and a mixed solvent thereof. As the base, there may be mentioned inorganic bases such as sodium hydrogen carbonate, sodium carbonate, potassium carbonate, cesium carbonate and the like or organic bases such as triethylamine, diethylamine, diisopropylamine, diisopropylethylamine, pyridine, and the like.

The compound of the formula (10) is synthesized from the compound of the formula (13)

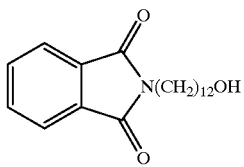
(13)

which is obtained from the compound of the formula (12)

HO(CH$_2$)$_{12}$OH (12).

The compound of the formula (12) is allowed to react with 0.2 to 2 equivalents of an azodicarboxylic acid esters, phosphines and phthalimide in a solvent at a temperature from −10° C. to 40° C. As the solvent, there may be mentioned dichloromethane, chloroform, carbon tetrachloride, tetrahydrofuran, ether, dioxane, benzene, acetonitrile, dimethylformamide, dimethyl sulfoxide and the like and a mixed solvent thereof. As the azodicarboxylic acid esters, there may be mentioned azodicarboxylic acid diethyl ester, azodicarboxylic acid diisopropyl ester and the like. As the phosphine, there may be mentioned triphenylphosphine, tributylphosphine and the like.

The compound of the formula (13) can be also prepared by reacting the compound of the formula (12) with hydrobromic acid to form 12-bromododecanol followed by reacting with potassium phthalimide.

The compound of the formula (13) thus obtained may be allowed to react with an acid, a base or hydrazine in a solvent at a temperature of 0° C. to a reflux temperature to prepare the compound of the formula (10). As the solvent, there may be mentioned dichloromethane, chloroform, carbon tetrachloride, tetrahydrofuran, ether, dioxane, benzene, acetonitrile, dimethylformamide, dimethyl sulfoxide, methanol, ethanol, acetic acid, water and the like and a mixed solvent thereof. As the acid, there may be mentioned hydrochloric acid, sulfuric acid, acetic acid, and the like and, as the base, sodium hydroxide, potassium hydroxide, and the like.

The compound of the formula (10) can be also synthesized by reducing the compound of the formula (14)

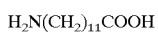
H$_2$N(CH$_2$)$_{11}$COOH (14)

or a derivative thereof such as an ester or Boc derivative thereof with LiAlH$_4$, BH$_3$ or the like.

The compound of the formula (15) obtained by converting to the Boc derivative an d su bsequent BH$_3$ reduction

BocNH(CH$_2$)$_{12}$OH (15)

may be also reacted with iodine, mesyl chloride or tosyl chloride and, if necessary, in the presence of a base or triphenylphosphine followed by deprotection of the Boc with an acid, thereby synthesizing the compound wherein X is an iodine atom, a mesyloxy group or a tosyloxy group.

Specific examples of the pyridinecarboxamide derivatives (1) of the present invention are given below:

N-(12-nitroxydodecyl)-6-(4-ethyl-1-piperazinyl)pyridine-3-carboxamide,

N-(12-nitroxydodecyl)-6-(4-isopropyl-1-piperazinyl) pyridine-3-carboxamide.

Specific examples of the compounds of the formula (2) are given below:

N-(12-hydroxydodecyl)-6-(4-ethyl-1-piperazinyl)pyridine-3-carboxamide,

N-(12-hydroxydodecyl)-6-(4-isopropyl-1-piperazinyl)
pyridine-3-carboxamide,
N-(12-iodododecyl)-6-(4-ethyl-1-piperazinyl)pyridine-3-
carboxamide,
N-(12-iodododecyl)-6-(4-isopropyl-1-piperazinyl)pyridine-3-carboxamide,
N-(12-bromododecyl)-6-(4-ethyl-1-piperazinyl)pyridine-3-
carboxamide,
N-(12-bromododecyl)-6-(4-isopropyl-1-piperazinyl)
pyridine-3-carboxamide,
N-(12-mesyloxydodecyl)-6-(4-ethyl-1-piperazinyl)
pyridine-3-carboxamide,
N-(12-mesyloxydodecyl)-6-(4-isopropyl-1-piperazinyl)-
pyridine-3-carboxamide,
N-(12-tosyloxydodecyl)-6-(4-ethyl-1-piperazinyl)pyridine-3-carboxamide,
N-(12-tosyloxydodecyl)-6-(4-isopropyl-1-piperazinyl)-
pyridine-3-carboxamide.

Specific examples of the compounds of the formula (7) are given below:

1-Ethylpiperazine, 1-isopropylpiperazine.

Specific examples of the compounds of the formula (9) are given below:

6-Chloronicotinic acid, 6-bromonicotinic acid.

Specific examples of the compounds of the formula (5) are given below:

12-Aminododecanol, 12-bromododecylamine, 12-iodododecylamine, 12-aminododecyl methanesulfonate, 12-aminododecyl p-toluenesulfonate.

Specific examples of the compounds of the formula (11) are given below:

6-Chloronicotinoyl chloride, 6-bromonicotinoyl chloride.

As the physiologically acceptable salts of the pyridinecarboxamide derivatives (1) of the present invention, there may be mentioned, for example, hydrochloride, sulfate, nitrate, hydrobromide, phosphate, maleate, fumarate, tartarate, malate, succinate, malonate, propionate, methanesulfonate, benzenesulfonate, p-toluenesulfonate, formate, acetate, trifluoroacetate and the like, and those compounds containing plural acidic functional groups such as carboxyl may be isolated in the form of an inorganic salt with a paired ion such as sodium, potassium, lithium, calcium, magnesium or the like.

A part of the pyridinecarboxamide derivatives represented by the formula (1) of this invention is metabolized and converted in vivo to a novel pyridine derivative which is effective in the treatment of cerebrovascular disorders. Main metabolic sites are listed below.

1) N-Oxidation at the 4-position of the piperazine ring and at the 1-position of the pyridine ring.
2) Hydroxylation of the piperazine ring, the pyridine ring and $(CH_2)_{12}$ and ring cleavage of the piperazine ring incidental to the hydroxylation.
3) Hydroxylation and dealkylation of the alkyl group at the 4-position of the piperazine ring.
4) Hydrolysis of the nitric ester and the pyridine-3-carboxamide.

Main metabolites are recited below:

N-(12-nitroxydodecyl)-6-(4-ethyl-1-piperazinyl)pyridine-3-carboxamide N-oxide,

N-(12-nitroxydodecyl)-6-(4-isopropyl-1-piperazinyl)-pyridine-3-carboxamide N-oxide.

The compounds (1) or pharmaceutically acceptable salts thereof according to the invention may be formulated to dosage forms such as tablets, granules, fine granules, powders, capsules, syrups, elixirs, suspensions, emulsions, injections and the like by incorporating suitable excipients, auxiliary agents, lubricants, antiseptics, disintegrating agents, buffer agents, binding agents, wetting agents, emulsifiers, coloring agents, corringents or flavors, and they may be administered orally or parenterally, preferably via intravenous injection or intravenous instillation.

In preparing a pharmaceutical preparation as drugs for internal use, the conventionally applicable auxiliaries such as lactose, sucrose, sorbitol, mannitol, potato starch, corn starch, cellulose derivatives, gelatin and the like are suitable as a carrier and lubricants such as magnesium stearate, Carbowax, polyethylene glycol and the like may be further added. The active compound in admixture with the above may be formed into granules, tablets, capsules and the like according to a conventional method.

In preparing a pharmaceutical preparation in the form of an aqueous preparation, the active ingredient may be dissolved in distilled water for injection and, as required, antioxidants, stabilizers, solubilizing agents, water-soluble surfactants, nonaqueous solvents, buffer agents, pH adjusters, preservatives, isotonic agents or soothing agents may be added and the resultant aqueous solution may be filtered, filled and sealed in a conventional manner and then sterilized by means of autoclaved sterilization or hot air sterilization to prepare injections.

In preparing a pharmaceutical preparation in the form of an emulsifiable injection, the sterilized active ingredient may be dissolved in a nonaqueous solvent and, if necessary, distilled water for injection, antioxidants, stabilizers, solubilizing agents, water-soluble surfactants, buffer agents, pH adjusters, preservatives, isotonic agents or soothing agents may be added and then the resultant emulsion may be filtered, filled and sealed in a conventional manner to prepare injections.

A dose of the compound or pharmaceutically acceptable salt thereof according to this invention may be selected depending upon the body weight, age, sex, lapsed time after onset, classification of diseases and others, and it is 1–1000 mg per day.

BEST MODE FOR CARRYING OUT THE INVENTION

This invention will be more specifically illustrated by way of the following Preparation Examples, Pharmacological Effect and Formulation Examples, but this invention is not intended to be limited thereto.

EXAMPLE 1

N-(12-Nitroxydodecyl)-6-(4-ethyl-1-piperazinyl)pyridine-3-carboxamide

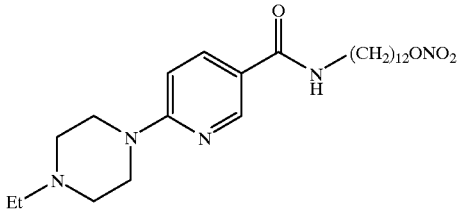

To 30 ml of fuming nitric acid cooled to −30° C. was gradually added 7.9 g of N-(12-hydroxydodecyl)-6-(4-ethyl-1-piperazinyl)pyridine-3-carboxamide over 30 minutes and the mixture was stirred at −30 to −20° C. for 40 minutes. The reaction solution was poured into ice, neutralized with sodium hydrogen carbonate and extracted with chloroform. The extract was dried over anhydrous sodium sulfate and distilled under reduced pressure. The residue thus obtained was chromatographed over a silica gel column and recystallized from methanol-water to afford the title compound as a crystal.

mp 71–72° C.

$^1$H NMR (CDCl$_3$)δ 1.13 (t, J=7.3 Hz, 3H), 1.27–1.42 (m, 16H), 1.59 (quint, J=6.8 Hz, 2H), 1.71 (quint, J=6.8 Hz, 2H), 2.46 (q, J=7.3 Hz, 2H), 2.54 (t, J=4.8 Hz, 4H), 3.42 (q, J=6.8 Hz, 2H), 3.66 (t, J=4.8 Hz, 4H), 4.44 (t, J=6.8 Hz, 2H), 5.94 (brs, 1H), 6.62 (d, J=9.2 Hz, 1H), 7.89 (dd, J=2.4, 9.2 Hz, 1H), 8.68 (d, J=2.4 Hz, 1H)

EXAMPLE 2

N-(12-Nitroxydodecyl)-6-(4-isopropyl-1-piperazinyl)pyridine-3-carboxamide

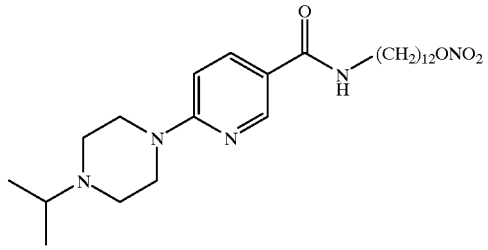

Synthesis was carried out in the same manner as in Example 1 using as a starting material N-(12-hydroxydodecyl)-6-(4-isopropyl-1-piperazinyl)pyridine-3-carboxamide. The title compound was obtained as a colorless crystal.

mp 56–58° C.

$^1$H NMR (CDCl$_3$)δ 1.08 (d, J=6.3 Hz, 6H), 1.26–1.36 (m, 16H), 1.57–1.60 (m, 2H), 1.67–1.73 (m, 2H), 1.61 (t, J=4.8 Hz, 4H), 2.73 (sept, J=6.3 Hz, 1H), 3.41 (q, J=6.8 Hz, 2H), 3.65 (t, J=4.8 Hz, 4H), 4.44 (t, J=6.8 Hz, 2H), 5.96 (brs, 1H), 6.61 (d, J=9.2 Hz, 1H),7.89 (dd, J=2.4, 8.7 Hz, 1H), 8.53 (d, J=2.4 Hz, 1H)

EXAMPLE 3

N-(12-Nitroxydodecyl)-6-(4-ethyl-1-piperazinyl)pyridine-3-carboxamide

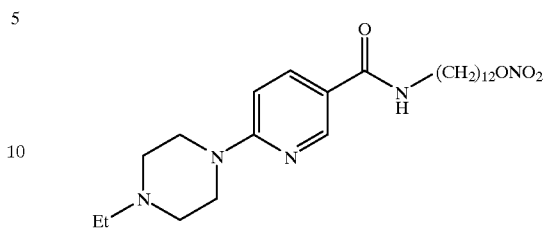

To a solution of 5.7 g of 12-aminododecyl nitrate hydrochloride in 80 ml of methylene chloride were added successively under ice-cooling 5.21 g of sodium 6-(4-ethylpiperazinyl)pyridine-3-carboxylate, 3.91 g of 1-hydroxybenzotriazole (HOBt) and 2.76 g of 1-ethyl-3-(3-dimethylaminopropyl)carbodiimide hydrochloride (WSCI) and then the mixture was stirred at room temperature overnight. The reaction solution was diluted with chloroform and washed successively with water, a saturated aqueous solution of sodium hydrogen carbonate and a saturated aqueous solution of sodium chloride, dried over anhydrous sodium sulfate and then distilled under reduced pressure. The residue thus obtained was chromatographed over a silica gel column to afford 8.56 g of the title compound as a crystal.

EXAMPLE 4

N-(12-Nitroxydodecyl)-6-(4-ethyl-1-piperazinyl)pyridine-3-carboxamide

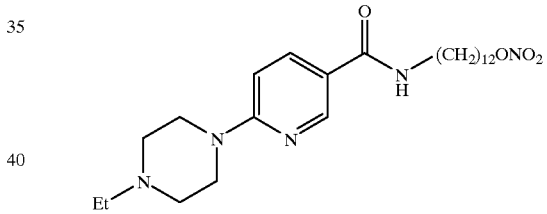

Preparation of Amberlyst A-26 (manufactrured by Rohm & Haas Co.) of a nitrate form 50 g of Amberlyst A-26 (Cl form) was washed successively with 300 ml each of methanol, water and a 2.5N aqueous solution of sodium hydroxide and 350 ml of ion exchanged water and then converted to the nitrate form with 300 ml of 1N-nitric acid. After the conversion, it was washed with ion exchanged water until it became neutral and then replaced with 200 ml of ethanol and 100 ml of acetone. The Amberlyst A-26 (a nitrate form) thus contained was dried at 50° C. under reduced pressure for 2 hours.

To a solution of 1.0 g of N-(12-mesyloxydodecyl)-6-(4-ethyl-1-piperazinyl)pyridine-3-carboxamide in toluene was added 4.0 g of Amberlyst A-26 (a nitrate form) and the mixture was heated under reflux for 3 hours. The ion exchange resin was filtered off and the filtrate was distilled off. The residue thus obtained was chromatographed over a silica gel column to afford 0.85 g of the title compound.

Similarly, the title compound was obtained using as a starting material N-(12-tosyloxydodecyl)-6-(4-ethyl-1-piperazinyl)pyridine-3-carboxamide, N-(12-iodododecyl)-6-(4-ethyl-1-piperazinyl)pyridine-3-carboxamide or N-(12-bromododecyl)-6-(4-ethyl-1-piperazinyl)pyridine-3-carboxamide.

13
EXAMPLE 5

N-(12-Nitroxydodecyl)-6-(4-ethyl-1-piperazinyl)pyridine-3-carboxamide

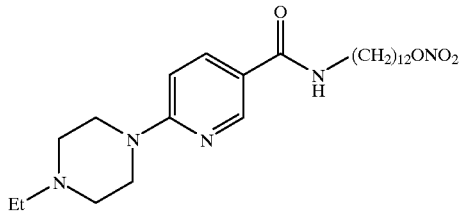

To a solution of 76 mg of N-(12-mesyloxydodecyl)-6-(4-ethyl-1-piperazinyl)pyridine-3-carboxamide in toluene was added 70 mg of tetrabutylammonium nitrate and the mixture was refluxed for 3 hours. To the reaction solution were added water and chloroform and the mixture was washed with a saturated aqueous solution of sodium chloride. The organic layer was dried over anhydrous magnesium sulfate and distilled off, and the residue thus obtained was chromatographed over a silica gel column to afford 63.1 mg of the title compound.

Similarly, the title compound was obtained using as a starting material N-(12-tosyloxydodecyl)-6-(4-ethyl-1-piperazinyl)pyridine-3-carboxamide, N-(12-iodododecyl)-6-(4-ethyl-1-piperazinyl)pyridine-3-carboxamide or N-(12-bromododecyl)-6-(4-ethyl-1-piperazinyl)pyridine-3-carboxamide.

EXAMPLE 6

N-(12-Nitroxydodecyl)-6-(4-ethyl-1-piperazinyl)pyridine-3-carboxamide

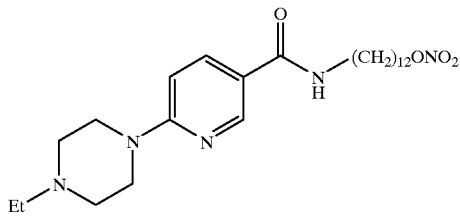

To a solution of 1.30 g of N-(12-iodododecyl)-6-(4-ethyl-1-piperazinyl)pyridine-3-carboxamide in toluene-acetonitrile was added 1.46 g of silver nitrate and the mixture was stirred at 35° C. for 3.5 hours. After the reaction solution was filtered, water and chloroform were added and the mixture was washed with a saturated aqueous solution of sodium chloride. The organic layer was dried over anhydrous magnesium sulfate and distilled off, and the residue thus obtained was chromatographed over a silica gel column to afford 1.11 g of the title compound.

Similarly, the title compound was obtained using as a starting material N-(12-bromododecyl)-6-(4-ethyl-1-piperazinyl)pyridine-3-carboxamide.

14
EXAMPLE 7

N-(12-Iodododecyl)-6-(4-ethyl-1-piperazinyl)pyridine-3-carboxamide

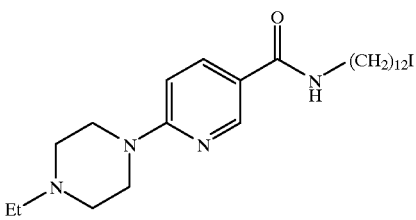

To a solution of 0.26 g of potassium iodide in 2 ml of phosphoric acid was added 0.10 g of N-(12-hydroxydodecyl)-6-(4-ethyl-1-piperazinyl)pyridine-3-carboxamide and the mixture was stirred at 110° C. for 3 hours. The reaction solution was diluted with water, and a saturated aqueous solution of sodium hydrogen carbonate and an aqueous solution of sodium thiosulfate were added. The mixture was extracted with chloroform. The organic layer was washed with water and then dried over anhydrous sodium sulfate. The solvent was distilled off under reduced pressure to afford 0.11 g of the title compound.

$^1$H NMR (CDCl$_3$)δ 1.13 (t, J=7.2 Hz, 3H), 1.27–1.38 (m, 16H), 1.56–1.60 (m, 2H), 1.82 (quint, J=7.1 Hz, 2H), 2.47 (q, J=7.2 Hz, 2H), 2.54 (t, J=5.1 Hz, 4H), 3.19 (t, J=7.1 Hz, 4H), 3.42 (q, J=6.7 Hz, 2H), 3.67(t, J=5.1 Hz, 4H), 5.90 (bs, 1H), 6.62 (d, J=8.8 Hz, 1H), 7.90 (dd, J=2.4 Hz, 8.8 Hz, 1H), 8.53 (d, J=2.4 Hz, 1H)

EXAMPLE 8

N-(12-Iodododecyl)-6-(4-ethyl-1-piperazinyl)pyridine-3-carboxamide

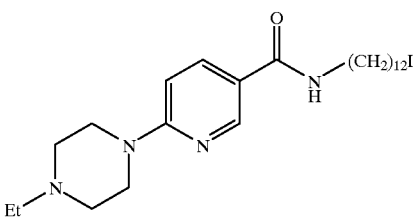

A solution of 2.09 g of N-(12-hydroxydodecyl)-6-(4-ethyl-1-piperazinyl)pyridine-3-carboxamide in 57% hydriodic acid was stirred at 120° C. for 30 minutes. The reaction solution was diluted with water and extracted with chloroform. The chloroform layer was washed with a saturated aqueous solution of sodium hydrogen carbonate and a saturated aqueous solution of sodium chloride, then dried over anhydrous magnesium sulfate. The solvent was distilled off under reduced pressure, and the residue thus obtained was chromatographed over a silica gel column to afford 1.94 g of the title compound.

EXAMPLE 9

N-(12-Bromododecyl)-6-(4-ethyl-1-piperazinyl)pyridine-3-carboxamide

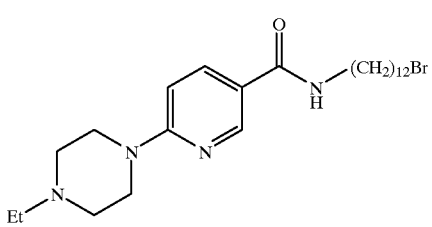

To a solution of 419 mg of N-(12-hydroxydodecyl)-6-(4-ethyl-1-piperazinyl)pyridine-3-carboxamide in 20 ml of toluene was added 0.60 ml of a 47% hydrobromic acid and the mixture was heated under reflux for one hour. The reaction solution was washed successively with water, a saturated aqueous solution of sodium hydrogen carbonate and a saturated aqueous solution of sodium chloride, dried over anhydrous magnesium sulfate. The solvent was distilled off under reduced pressure, and the residue thus obtained was chromatographed over a silica gel column to afford 400 mg of the title compound.

$^1$H NMR (CDCl$_3$)δ 1.13 (t, J=7.2 Hz, 3H), 1.27–1.44 (m, 16H), 1.56–1.63 (m, 2H), 1.85 (quint, J=7.2 Hz, 2H), 2.47 (q, J=7.2 Hz, 2H), 2.54 (t, J=5.1 Hz, 4H), 3.39–3.45 (m, 4H), 3.67 (t, J=5.1 Hz, 4H), 5.90 (bs, 1H), 6.62 (d, J=8.8 Hz, 1H), 7.90 (dd, J=2.4 Hz, 8.8 Hz, 1H), 8.53 (d, J=2.4 Hz, 1H)

EXAMPLE 10

N-(12-Iodododecyl)-6-(4-ethyl-1-piperazinyl)pyridine-3-carboxamide

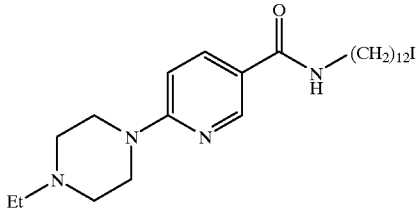

To 170 mg of 12-iodododecylamine hydroiodide were added 120 mg of sodium 6-(4-ethyl-1-piperazinyl)-pyridine-3-carboxylate, 10 ml of methylene chloride, 95 mg of 1,3-dicyclohexylcarbodiimide (DCC) and 12 mg of 1-hydroxybenzotriazole (HOBt) and the mixture was stirred at room temperature for 3 hours. Insolubles were filtered off and the filtrate was chromatographed over a silica gel column to afford 169.5 mg of the title compound.

EXAMPLE 11

N-(12-Iodododecyl)-6-(4-ethyl-1-piperazinyl)pyridine-3-carboxamide

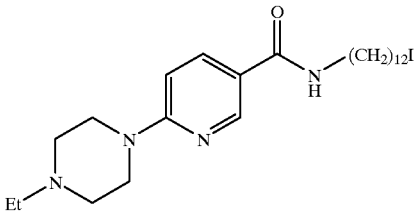

To a suspension of 0.20 g of sodium 6-(4-ethyl-1-piperazinyl)pyridine-3-carboxylate in 10 ml of methylene chloride was added 0.2 ml of oxalyl chloride and the mixture was heated under reflux for one hour. The reaction solution was distilled off under reduced pressure and 10 ml of methylene chloride was added to the residue. 0.3 ml of triethylamine and 0.17 g of 12-iodododecylamine hydrochloride were further added and the mixture was stirred overnight. The reaction solution was diluted with chloroform and washed successively with a 1N aqueous solution of sodium hydroxide, water and a saturated aqueous solution of sodium chloride, dried over anhydrous sodium sulfate. The solvent was distilled off, and the residue thus obtained was chromatographed over a silica gel column to afford 0.21 g of the title compound.

EXAMPLE 12

N-(12-Iodododecyl)-6-(4-ethyl-1-piperazinyl)pyridine-3-carboxamide

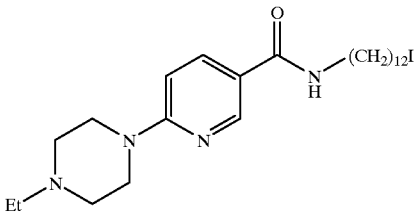

To a solution of 72 mg of N-(12-mesyloxydodecyl)-6-(4-ethyl-1-piperazinyl)pyridine-3-carboxamide in acetone was added 130 mg of sodium iodide and the mixture was heated under reflux for 10 hours. To the reaction solution were added water and chloroform and extracted with chloroform. The chloroform layer was washed with a saturated aqueous solution of sodium chloride and then dried over anhydrous magnesium sulfate. The solvent was then distilled off under reduced pressure. The residue thus obtained was chromatographed over a silica gel column to afford 69.0 mg of the title compound.

Similarly, the title compound was obtained using as a starting material N-(12-tosyloxydodecyl)-6-(4-ethyl-1-piperazinyl)pyridine-3-carboxamide.

EXAMPLE 13

N-(12-Mesyloxydodecyl)-6-(4-ethyl-1-piperazinyl)pyridine-3-carboxamide

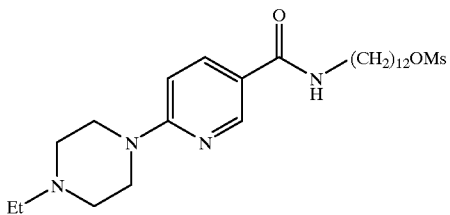

To a solution of 3.77 g of 12-aminododecyl methanesulfonate hydrochloride in 100 ml of methylene chloride were added successively under ice-cooling 3.60 g of sodium 6-(4-ethyl-1-piperazinyl)pyridine-3-carboxylate, 2.89 g of 1-hydroxybenzotriazole (HOBt), 1.99 g of 1-ethyl-3-(3-dimethylaminopropyl)carbodiimide hydrochloride (WSCI) and then the mixture was stirred overnight. The reaction solution was diluted with chloroform and washed successively with water, a saturated aqueous solution of sodium hydrogen carbonate and a saturated aqueous solution of sodium chloride, dried over anhydrous sodium sulfate and then distilled under reduced pressure. The residue thus obtained was chromatographed over a silica gel column to afford 4.96 g of the title compound.

$^1$H NMR (CDCl$_3$)δ 1.13 (t, J=7.3 Hz, 3H), 1.27–1.33 (m, 16H), 1.57 –1.61 (m, 2H), 1.75 (quint, J=7.2 Hz, 2H), 2.47 (q, J=7.3 Hz, 2H), 2.54 (t, J=5.1 Hz, 4H), 3.00 (s, 3H), 3.42 (q, J=6.6 Hz, 2H), 3.67 (t, J=5.1 Hz, 4H), 4.22 (t, J=6.6 Hz, 2H), 5.92 (bs, 1H), 6.62 (d, J=8.8 Hz, 1H), 7.90 (dd, J=2.4 Hz, 8.8 Hz, 1H), 8.53 (d, J=2.4 Hz, 1H)

EXAMPLE 14

N-(12-Tosyloxydodecyl)-6-(4-ethyl-1-piperazinyl)pyridine-3-carboxamide

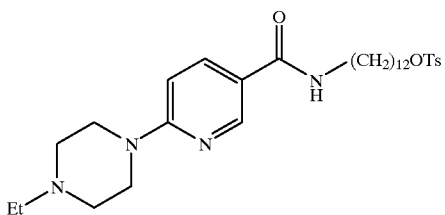

To a suspension of 210 mg of N-(12-hydroxydodecyl)-6-(4-ethyl-1-piperazinyl)pyridine-3-carboxamide in 10 ml of methylene chloride were added 0.03 ml of pyridine, 115 mg of tosyl chloride and a catalytic amount of 4-dimethylaminopyridine and the mixture was stirred at room temperature for one hour. The reaction solution was washed with water and a saturated aqueous solution of sodium chloride and then dried over anhydrous magnesium sulfate. The solvent was distilled off under reduced pressure and the residue thus obtained was chromatographed over a silica gel column to afford 219 mg of the title compound.

$^1$H NMR (CDCl$_3$)δ 1.14 (t, J=7.2 Hz, 3H), 1.21–1.26 (m, 16H), 1.57 –1.65 (m, 4H), 2.45 (s, 3H), 2.46–2.50 (m, 16H), 2.55 (t, J=5.2 Hz, 4H), 3.42 (q, J=6.6 Hz, 2H), 3.67 (t, J=5.2 Hz, 4H), 4.02 (t, J=6.3 Hz, 2H), 5.94 (bs, 1H), 6.62 (d, J=8.8 Hz, 1H), 7.34 (d, J=8.3 Hz, 2H), 7.78 (d, J=8.3 Hz, 2H), 7.89 (dd, J=2.4 Hz, 8.8 Hz, 1H), 8.53 (d, J=2.4 Hz, 1H)

EXAMPLE 15

N-(12-Mesyloxydodecyl)-6-(4-ethyl-1-piperazinyl)pyridine-3-carboxamide

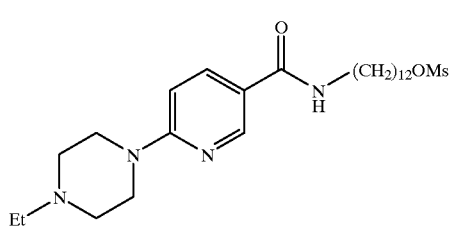

To a solution of 1.26 g of N-(12-hydroxydodecyl)-6-(4-ethyl-1-piperazinyl)pyridine-3-carboxamide in 20 ml of chloroform were added 4.2 ml of triethylamine, 5 ml of pyridine and 1.0 ml of mesyl chloride and the mixture was stirred at room temperature for 30 minutes. The reaction solution was washed successively with water, 3N-hydrochloric acid and a saturated aqueous solution of sodium chloride and then dried over anhydrous magnesium sulfate. The solvent was distilled off under reduced pressure and the residue thus obtained was chromatographed over a silica gel column to afford 1.11 g of the title compound.

EXAMPLE 16

12-Aminododecyl Nitrate Hydrochloride

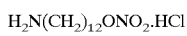

To 12 ml of fuming nitric acid was added at −20° C. 3.0 g of 12-aminododecanol and the mixture was stirred for 30 minutes. The reaction solution was poured into ice-water and extracted with chloroform. The extract was washed successively with a saturated aqueous solution of sodium hydrogen carbonate and a saturated aqueous solution of sodium chloride, dried over anhydrous sodium sulfate. Then 3.7 ml of a hydrogen chloride-ethyl acetate solution was added under ice-cooling and distilled under reduced pressure. The residue thus obtained was recrystallized from chloroform-hexane to afford 3.03 g of the title compound.

$^1$H NMR (CDCl$_3$)δ 1.20–1.42 (m, 16H), 1.68–1.80 (m, 4H), 2.94–3.01 (m, 2H), 4.44 (t, J=6.8 Hz, 2H), 8.22–8.33 (brs, 3H)

PREPARATION EXAMPLE 1

N-(12-Hydroxydodecyl)-6-(4-ethyl-1-piperazinyl)pyridine-3-carboxamide

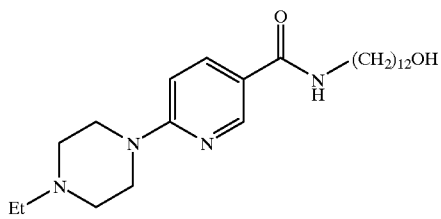

To 0.6 g of N-(12-hydroxydodecyl)-6-chloropyridine-3-carboxamide was added 5 ml of 1-ethylpiperazine and the mixture was stirred at 160° C. for 30 minutes. The reaction solution was diluted with chloroform, washed with water, dried over anhydrous sodium sulfate and distilled off under reduced pressure. The residue was chromatographed over a silica gel column to afford the title compound.

mp 108.5–110° C.

$^1$H NMR (CDCl$_3$)δ 1.13 (t, J=7.3 Hz, 3H), 1.27–1.32 (m, 16H), 1.52–1.63 (m, 4H), 2.47 (q, J=7.3 Hz, 2H), 2.54 (t, J=4.8 Hz, 4H), 3.42 (q, J=6.8 Hz, 2H), 3.62–3.67 (m, 6H), 5.93 (brs, 1H), 6.62 (d, J=8.7 Hz, 1H), 7.90 (dd, J=2.4, 8.7 Hz, 1H), 8.53 (d, J=2.4 Hz, 1H)

PREPARATION EXAMPLE 2

N-(12-Hydroxydodecyl)-6-(4-isopropyl-1-piperazinyl)pyridine-3-carboxamide

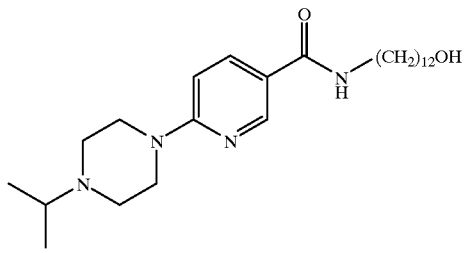

To 2.78 g of N-(12-hydroxydodecyl)-6-chloropyridine-3-carboxamide was added 4.15 g of 1-isopropylpiperazine and the mixture was stirred at 160° C. for 30 minutes. The reaction solution was diluted with chloroform, washed with water, dried over anhydrous sodium sulfate and distilled off under reduced pressure. The residue was chromatographed over a silica gel column to afford 2.2 g of the title compound as a crystal.

$^1$H NMR (CDCl$_3$)δ 1.08 (d, J=6.8 Hz, 6H), 1.27–1.32 (m, 16H), 1.52–1.65 (m, 4H), 2.61 (t, J=4.8 Hz, 4H), 2.73 (7th, J=6.8 Hz, 1H), 3.42 (q, J=6.8 Hz, 2H), 3.62–3.66 (m, 6H), 5.92 (brs, 1H), 6.61 (d, J=8.7 Hz, 1H), 7.89 (dd, J=2.4, 8.7 Hz, 1H), 8.52 (d, J=2.4 Hz, 1H)

PREPARATION EXAMPLE 3

N-(12-Hydroxydodecyl)-6-(4-ethyl-1-piperazinyl)pyridine-3-carboxamide

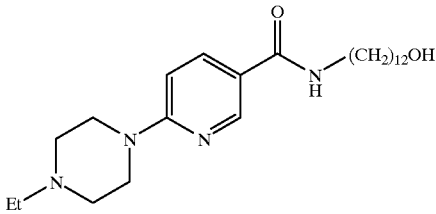

PREPARATION EXAMPLE 3-1

6-(4-Ethyl-1-piperazinyl)pyridine-3-carboxamide

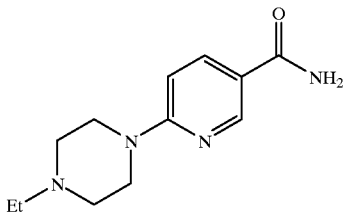

A mixture of 0.5 g of 6-chloronicotinamide and 3 ml of 1-ethylpiperazine was stirred at 110° C. for 2 hours. The reaction solution was diluted with ethyl acetate, washed with water and then dried over anhydrous sodium sulfate. The solvent was distilled off under reduced pressure to afford 0.10 g of the title compound.

$^1$H NMR (CDCl$_3$)δ 1.13 (t, J=7.3 Hz, 3H), 2.46 (q, J=7.3 Hz, 2H), 2.54 (t, J=5.3 Hz, 4H), 3.69 (t, J=5.3 Hz, 4H), 5.60–5.80 (brs, 2H), 6.63 (d, J=8.7 Hz, 1H), 7.93 (dd, J=2.4, 8.7 Hz, 1H), 8.58 (d, J=2.4 Hz, 1H)

PREPARATION EXAMPLE 3-2

N-(12-Hydroxydodecyl)-6-(4-ethyl-1-piperazinyl)pyridine-3-carboxamide

To a suspension of 0.055 g of 6-(4-ethyl-1-piperazinyl)pyridine-3-carboxamide, 0.011 g of tetrabutylammonium hydrogen sulfate, 0.11 g of sodium hydroxide and 0.05 g of potassium carbonate in 3 ml of toluene was added dropwise at 70° C. a solution of 12-bromododecanol in 2 ml of toluene and the mixture was stirred at 70° C. for 13 hours. The reaction solution was diluted with chloroform, washed with water and a saturated aqueous solution of sodium chloride, dried over anhydrous sodium sulfate. The solvent was distilled off under reduced pressure. The residue thus obtained was chromatographed over a silica gel column to afford 0.025 g of the title compound.

PREPARATION EXAMPLE 4

N-(12-Hydroxydodecyl)-6-(4-isopropyl-1-piperazinyl)pyridine-3-carboxamide

PREPARATION EXAMPLE 4-1

N-(12-Hydroxydodecyl)-6-(1-piperazinyl)pyridine-3-carboxamide

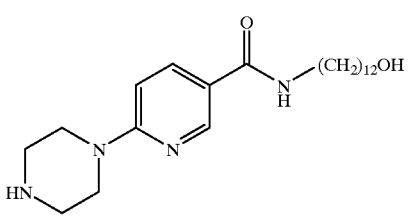

To a suspension of 2.38 g of N-( 12-hydroxydodecyl)-6-chloropyridine-3-carboxamide in 50 ml of toluene was added 3.0 g of piperadine and the mixture was heated under reflux for 10 hours and then the reaction solution was distilled under reduced pressure. The residue thus obtained was chromatographed over a silica gel column to afford the title compound as a pale yellow crystal.

$^1$H NMR (CDCl$_3$)δ 1.27–1.33 (m, 16H), 1.52–1.61 (m, 4H), 2.97 (t, J=4.8 Hz, 4H), 3.42 (q, J=6.8 Hz, 2H), 3.59–3.65 (m, 6H), 5.92 (brs,1H), 6.61 (d, J=8.7 Hz, 1H), 7.90 (dd, J=2.7, 8.7 Hz, 1H), 8.53 (d, J=2.4 Hz, 1H)

PREPARATION EXAMPLE 4-2

N-(12-Hydroxydodecyl)-6-(4-isopropyl-1-piperazinyl)pyridine-3-carboxamide

A solution of 0.7 g of N-(12-hydroxydodecyl)-6-(1-piperazinyl)pyridine-3-carboxamide, 0.24 g of isopropyl bromide and 0.7 g of potassium carbonate in 20 ml of dimethylformamide was stirred at 100° C. for 3 hours. The reaction solution was diluted with chloroform, washed with water and a saturated aqueous solution of sodium chloride, dried over anhydrous sodium sulfate. The solvent was distilled off under reduced pressure. The residue thus obtained was chromatographed over a silica gel column to afford the title compound as a crystal.

PREPARATION EXAMPLE 5

N-(12-Hydroxydodecyl)-6-(4-ethyl-1-piperazinyl)pyridine-3-carboxamide

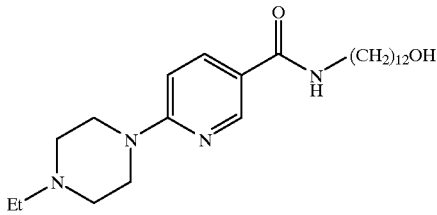

To 4.07 g of potassium 6-(4-ethyl-1-piperazinyl)-pyridine-3-carboxylate and 3.00 g of 12-aminododecanol was added 50 ml of chloroform and then 2.01 g of 1-hydroxybenzotriazole (HOBt) and 3.07 g of 1,3-dicyclohexylcarbodiimide (DCC) were added thereto while stirring at room temperature and then the mixture was stirred at room temperature for 17 hours. A further 50 ml of chloroform was added, the mixture was stirred and then insolubles were filtered off. After the residue on a filter paper was washed with chloroform, the washing and the chloroform solution were combined and washed with a 10% aqueous solution of sodium hydroxide and dried over anhydrous magnesium sulfate. After the chloroform solution was concentrated, diisopropyl ether was added and the crystal thus separated out was recovered by filtration and dried under reduced pressure to afford 5.10 g of the title compound as a crystal.

PREPARATION EXAMPLE 6

N-(12-Hydroxydodecyl)-6-(4-ethyl-1-piperazinyl)pyridine-3-carboxamide

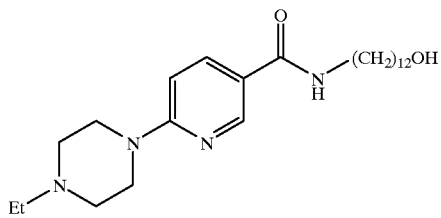

To 4.07 g of potassium 6-(4-ethyl-1-piperazinyl)-pyridine-3-carboxylate and 3.00 g of 12-aminododecanol was added 50 ml of methylene chloride and then 2.86 g of 1-ethyl-3-(3-dimethylaminopropyl)carbodiimide hydrochloride (WSCI) and 2.01 g of 1-hydroxybenzotriazole (HOBt) were added while stirring at room temperature. The mixture was stirred at room temperature for 15 hours. To the reaction solution were added water and diisopropyl ether and subsequent filtration and drying under reduced pressure afforded 5.67 g of the title compound as a crystal.

PREPARATION EXAMPLE 7

N-(12-Hydroxydodecyl)-6-(4-ethyl-1-piperazinyl)pyridine-3-carboxamide

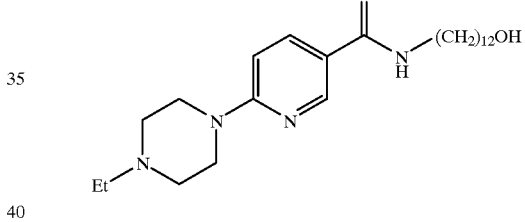

To a suspension of 0.22 g of sodium 6-(4-ethyl-1-piperazinyl)pyridine-3-carboxylate in 10 ml of methylene chloride were added 0.2 ml of oxalyl chloride and the mixture was heated under reflux for one hour. The reaction solution was distilled off under reduced pressure, to the residue were added 10 ml of methylene chloride, 0.3 ml of triethylamine and 0.15 g of 12-aminododecanol and the mixture was stirred overnight. The reaction solution was diluted with chloroform, washed successively with a 1N aqueous solution of sodium hydroxide, water and a saturated aqueous solution of sodium chloride and then dried over anhydrous sodium sulfate. The solvent was distilled off and the residue thus obtained was chromatographed over a silica gel column to afford 0.21 g of the title compound.

PREPARATION EXAMPLE 8

12-Iodododecylamine hydroiodide

An aqueous solution of 100 mg of 12-aminododecanol in 57% hydriodic acid was heated under reflux for one hour. To the reaction solution was added chloroform and the mixture was washed successively with water, a 10% aqueous solution of sodium thiosulfate and a saturated aqueous solution of sodium chloride and then dried over anhydrous magnesium sulfate. The solvent was distilled off and the residue thus obtained was chromatographed over a silica gel column to afford 171 mg of the title compound.

$^1$H NMR (CDCl$_3$)δ 1.27–1.39 (m, 16H), 1.65 (bs, 2H), 1.73–1.86 (m, 4H), 2.98 (t, J=7.8 Hz, 2H), 3.19 (t, J=7.1 Hz, 2H), 8.21 (bs, 1H), 6.62 (d, J=8.8 Hz, 1H)

PREPARATION EXAMPLE 9

12-Aminododecanol

In 600 ml of methanol was dissolved while warming 48.0 g of N-(12-hydroxydodecyl)phthalimide, 50 ml of hydrazine monohydrate was added at room temperature with stirring and the mixture was stirred overnight. The crystal thus separated out was filtered off and the solvent was distilled off. The residue was extracted with hot chloroform and insolubles were filtered off. The filtrate was distilled, the residue was extracted with hot chloroform (100 ml×3) and then the solvent was distilled off. The residue was dissolved in methanol and recrystallization from methanol-ethyl acetate gave 21.6 g of the title compound as a crystal.

$^1$H NMR (CDCl$_3$)δ 1.22–1.47 (m, 16H), 1.43 (quint, J=7 Hz, 2H), 1.56 (quint, J=7 Hz, 2H), 2.68 (q, J=7 Hz, 2H), 3.64 (t, J=7 Hz, 2H)

PREPARATION EXAMPLE 10

N-(12-Hydroxydodecyl)phthalimide

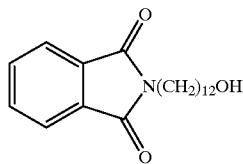

To a solution of 45 g of 12-bromododecanol in 500 ml of dimethylformamide was added 75 g of potassium phthalimide and the mixture was stirred at 100° C. for 3 hours. After completion of the reaction, the solvent was distilled off and the residue was dispersed with water. The crude crystal thus separated out was recovered by filtration and recrystallized from methanol to afford 54 g of the title compound as a crystal.

$^1$H NMR (CDCl$_3$)δ 1.19–1.41 (m, 16H), 1.56 (quint, J=7 Hz, 2H), 1.67 (quint, J=7 Hz, 2H), 3.64 (q, J=6 Hz, 2H), 3.68 (t, J=7 Hz, 2H), 7.71 (dd, J=3 Hz, 5 Hz, 2H), 7.84 (dd, J=3 Hz, 5 Hz, 2H)

PREPARATION EXAMPLE 11

12-Bromododecanol

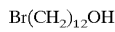

To 30.25 g of 1,12-dodecanediol were added 350 ml of toluene and 52 ml of 48% hydrobromic acid and the mixture was heated under reflux under azeotropic condition for 2 hours. The reaction solution was cooled and the starting material precipitated out was filtered off. The filtrate was distilled and recrystallized from hexane to afford 30.2 g of the title compound as a crystal.

PREPARATION EXAMPLE 12

12-Aminododecanol hydrochloride

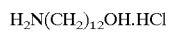

To a suspension of 5.0 g of tert-butyl N-(12-hydroxydodecyl)carbamate in 25 ml of methanol was added 3 ml of hydrochloric acid and the mixture was heated under reflux for one hour. The reaction solution was distilled off under reduced pressure, ethyl acetate was added to the residue, the crystal thus precipitated out was recovered by filtration and dried under reduced pressure to afford 3.23 g of the title compound.

$^1$H NMR (CD$_3$OD)δ 1.28–1.40 (m, 16H), 1.51 (quint, J=6.8 Hz, 2H), 1.63 (quint, J=7.3 Hz, 2H), 2.89 (t, J=7.8 Hz, 2H), 3.52 (t, J=6.8 Hz, 2H)

PREPARATION EXAMPLE 13

12-Aminododecyl methanesulfonate hydrochloride

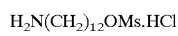

To a solution of 8.06 g of tert-butyl N-(12-mesyloxydodecyl)carbamate in 60 ml of ethyl acetate was added 10 ml of hydrochloric acid under ice-cooling and the mixture was stirred at room temperature for one hour. The reaction solution was cooled with ice, hexane was added, the crystal thus precipitated out was recovered by filtration and dried under reduced pressure to afford the title compound.

$^1$H NMR (CDCl$_3$)δ 1.23–1.42 (m, 16H), 1.71–1.83 (m, 4H), 2.94–3.01 (m, 2H), 3.00 (s, 3H), 4.22 (t, J=6.3 Hz, 2H), 8.19–8.27 (brs, 3H)

PREPARATION EXAMPLE 14 tert-Butyl N-(12-mesyloxydodecyl)carbamate

To a solution of 8.96 g of tert-butyl N-(12-hydroxydodecyl)carbamate in 60 ml of tetrahydrofuran were successively added dropwise under ice-cooling 2.1 ml of mesyl chloride and 3.8 ml of triethylamine and the mixture was stirred for one hour. To the reaction solution was added ethyl acetate and the mixture was washed successively with water, a saturated aqueous solution of sodium hydrogen carbonate, water and a saturated aqueous solution of sodium chloride, dried over anhydrous sodium sulfate and the solvent was distilled off under reduced pressure to afford 8.06 g of the title compound.

$^2$H NMR (CDCl$_3$)δ 1.23–1.47 (m, 18H), 1.44 (s, 9H), 1.71–1.78 (m, 2H), 3.00 (s, 3H), 3.07–3.12 (m, 2H), 4.22 (t, J=6.3 Hz, 2H), 4.45–4.51 (m, 1H)

PREPARATION EXAMPLE 15

12-Iodododecylamine hydrochloride

To a solution of 0.33 g of tert-butyl N-(12-iodododecyl) carbamate in 25 ml of ethyl acetate was added 2.6 ml of hydrochloric acid and the mixture was stirred for 0.5 hour. The reaction solution was distilled off under reduced pressure. The residue was dissolved in chloroform, washed with water and then dried over anhydrous sodium sulfate. The solvent was distilled off under reduced pressure. Crystallization from ethyl acetate and hexane afforded 0.17 g of the title compound.

$^1$H NMR (CDCl$_3$)δ 1.20–1.43 (m, 16H), 1.70–1.85 (m, 4H), 2.92–3.02 (m, 2H), 3.19 (t, J=7.3 Hz, 2H), 8.13–8.35 (m, 3H)

PREPARATION EXAMPLE 16 tert-Butyl N-(12-iodododecyl)carbamate

To a suspension of 0.5 g of tert-butyl N-(12-hydroxydodecyl)carbamate in 15 ml of toluene were added 0.28 g of imidazole, 1.09 g of triphenylphosphine and 0.84 g of iodine and the mixture was stirred for 0.5 hour. Then, 5 ml of tetrahydrofuran was further added and the mixture was stirred for 2 hours. To the reaction solution was added ethyl acetate and the mixture was washed successively with a 10% aqueous solution of sodium thiosulfate and water and dried over anhydrous sodium sulfate and the solvent was distilled off under reduced pressure. The residue thus obtained was chromatographed over a silica gel column to afford 0.42 g of the title compound.

$^1$H NMR (CDCl$_3$)δ 1.23–1.47 (m, 18H), 1.44 (s, 9H), 1.81 (quint, J=7.3 Hz, 2H), 2.99–3.12 (m, 2H), 3.18 (t, J=7.3 Hz, 2H), 4.45–4.53 (m,1H)

PREPARATION EXAMPLE 17 tert-Butyl N-(12-hydroxydodecyl)carbamate

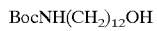

To a suspension of 1.2 g of sodium borohydride in 10 ml of tetrahydrofuran (THF) were added under ice-cooling a solution of 3.6 g of iodine in 20 ml of THF and the mixture was stirred for one hour. Then, a solution of 7.5 g of 12-(tert-butoxycarboxamido)dodecanoic acid in 25 ml of THF was added dropwise and the mixture was stirred at room temperature for one hour. To the reaction solution were added successively water and an aqueous solution of citric acid and extracted with ethyl acetate. The organic layer was washed successively with an aqueous solution of citric acid, a 1N-sodium hydroxide solution, water and a saturated aqueous solution of sodium chloride and dried over anhydrous sodium sulfate. The solvent was distilled off under reduced pressure. The residue thus obtained was recrystallized from ethyl acetate-hexane to afford 4.7 g of the title compound.

$^1$H NMR (CDCl$_3$)δ 1.23–1.47 (m, 18H), 1.44 (s, 9H), 1.56 (quint, J=7.3 Hz, 2H), 3.07–3.12 (m, 2H), 3.64 (t, J=6.8 Hz, 2H), 4.45–4.53 (m, 1H)

PREPARATION EXAMPLE 18

12-(tert-Butoxycarboxamido)dodecanoic acid

To 2.15 g of 12-aminododecanoic acid were added 20 ml of dioxane and 10 ml of water and then 2.39 g of di-tert-butyl dicarbonate and 10 ml of an aqueous 1N-sodium hydroxide solution were added under ice-cooling. The mixture was stirred at room temperature overnight. The reaction solution was distilled off under reduced pressure, the residue was made acidic by the addition of a 10% aqueous solution of citric acid and extracted with ethyl acetate. The organic layer was washed successively with water and a saturated aqueous solution of sodium chloride and dried over anhydrous sodium sulfate. The solvent was distilled off under reduced pressure to afford 3.09 g of the title compound.

$^1$H NMR (CDCl$_3$)δ 1.22–1.49 (m, 16H), 1.44 (s, 9H), 1.59–1.64 (m, 2H), 2.34 (t, J=7.3 Hz, 2H), 3.05–3.12 (m, 2H), 4.49–4.54 (m, 1H)

PREPARATION EXAMPLE 19

Sodium 6-(4-ethyl-1-piperazinyl)pyridine-3-carboxylate

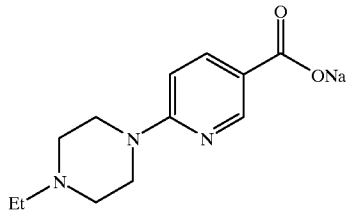

A solution of 3.1 g of sodium hydroxide in 15 ml of water was added to 75 ml of methanol. 15 g of methyl 6-(4-ethyl-1-piperazinyl)pyridine-3-carboxylate was added and the mixture was heated under reflux for 1.5 hours. The solvent was distilled off under reduced pressure, to the resulting residue was added hot acetone and the crystal thus precipitated out was recovered by filtration. It was again washed with hot acetone to afford 17.2 g of the title compound as a crystal.

PREPARATION EXAMPLE 20

Potassium 6-(4-ethyl-1-piperazinyl)pyridine-3-carboxylate

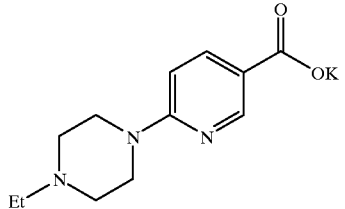

To a solution of 69.81 g of ethyl 6-(4-ethyl-1-piperazinyl) pyridine-3-carboxylate in 280 ml of methanol were added 37 g of potassium hydroxide and a small volume of water and the mixture was heated under reflux for one hour. To the reaction solution were added methanol and isopropyl alcohol, the crystal thus precipitated out was recovered by filtration and then dried under reduced pressure to afford 70.65 g of the title compound as a colorless crystal.

$^1$H NMR (CD$_3$OD)δ 1.14 (t, J=7.2 Hz, 3H), 2.48 (q, J=7.2 Hz, 2H), 2.58 (t, J=5.1 Hz, 4H), 3.61 (t, J=5.1 Hz, 4H), 6.75 (d, J=8.8 Hz, 1H), 8.05 (dd, J=2.4 Hz, 8.8 Hz, 1H), 8.69 (d, J=2.4 Hz, 1H)

PREPARATION EXAMPLE 21

Methyl 6-(4-ethyl-1-piperazinyl)pyridine-3-carboxylate

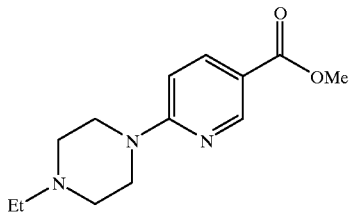

To 100 g of 1-ethylpiperazine warmed to 80° C. was added at 80–100° C. with stirring 50 g of methyl 6-chloropyridine-3-carboxylate. To the reaction solution was added 0.5 l of water and the mixture was stirred. The crystal thus precipitated out was recovered by filtration, dried under reduced pressure to afford 68.8 g of the title compound as a crystal.

PREPARATION EXAMPLE 22

Ethyl 6-(4-ethyl-1-piperazinyl)pyridine-3-carboxylate

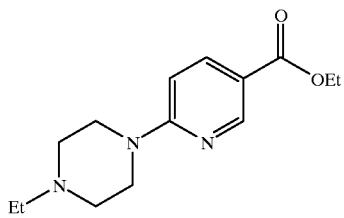

To 55.69 g of ethyl 6-chloropyridine-3-carboxylate was added 115 ml of 1-ethylpiperazine and the mixture was heated with stirring (55–137° C.) for 5 minutes. After completion of the reaction, the 1-ethylpiperazine was distilled off under reduced pressure, the residue was crystallized from water-metanol. The crystal was washed with water and then dried under reduced pressure to afford 71.89 g of the title compound as a colorless crystal.

$^1$H NMR (CDCl$_3$)δ 1.13(t, J=7.2 Hz, 3H), 1.36 (t, J=7.1 Hz, 3H), 2.47 (q, J=7.2 Hz, 2H), 2.54 (t, J=5.1 Hz, 4H), 3.71 (t, J=5.1 Hz, 4H), 4.33 (q, J=7.1 Hz, 2H), 6.58 (d, J=8.8 Hz, 1H), 8.02 (dd, J=2.4 Hz, 8.8 Hz, 1H), 8.80 (d, J=2.4 Hz, 1H)

PREPARATION EXAMPLE 23

1-Isopropylpiperazine

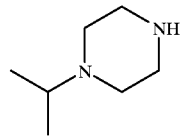

PREPARATION EXAMPLE 23-1

1-Acetyl-4-isopropylpiperazine

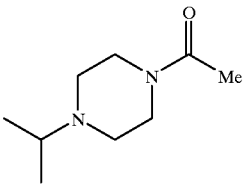

To 12.95 g of piperazine, 0.75 g of sodium iodide and 3.46 g of potassium carbonate were added successively 25 ml of methanol and 6.15 g of 2-bromopropane and the mixture was stirred at 60° C. for 4 hours. After the addition of chloroform and washing with a saturated aqueous solution of sodium chloride, the mixture was dried over anhydrous magnesium sulfate. The solvent was distilled off under reduced pressure, 12 ml of acetic anhydride was slowly added and the mixture was stirred at room temperature for 2.5 hours. The reaction solution was poured into ice and chloroform was added and the mixture was neutralized with sodium carbonate. After extracting with chloroform, the extract was dried over anhydrous magnesium sulfate. The solvent was distilled off under reduced pressure and the residue thus obtained was chromatographed over a silica gel column. The solvent was distilled off and the residue was allowed to stand overnight. The diacetylpiperazine thus precipitated out was filtered off to afford 7.26 g of the title compound as an oily substance.

$^1$H NMR (CDCl$_3$)δ 1.04 (d, J=6 Hz, 6H), 2.08 (s, 3H), 2.47 (t, J=5 Hz,2H), 2.51 (t, J=5 Hz, 2H), 2.71 (sept, J=6 Hz, 1H), 3.46 (t, J=5 Hz, 2H), 3.62 (t, J=5 Hz, 2H)

PREPARATION EXAMPLE 23-2

1-Isopropylpiperazine

To 7.26 g of 1-acetyl-4-isopropylpiperazine were added 100 ml of methanol and 10 g of potassium hydroxide and the mixture was heated under reflux for 17 hours. After the solvent was distilled off, water and chloroform were added. The mixture was extracted with chloroform and dried over anhydrous magnesium sulfate. The solvent was distilled off under reduced pressure to afford 5.78 g of the title compound as an oily substance.

$^1$H NMR (CDCl$_3$)δ 1.05 (d, J=6 Hz, 6H), 2.49 (bt, J=5 Hz, 4H), 2.75 (sept, J=6 Hz, 1H), 2.90 (t, J=5 Hz, 4H)

PREPARATION EXAMPLE 24

1-Isopropylpiperazine

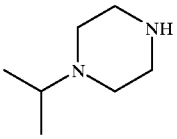

1-Formyl-4-isopropylpiperazine

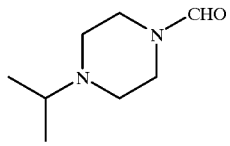

To a solution of 1.02 g of formylpiperazine in 90 ml of acetone was added 0.1 g of 5% palladium carbon and the mixture was stirred under hydrogen atmosphere for 60 hours. The catalyst was filtered off and distilled off under reduced pressure to afford 1.31 g of the title compound.

$^1$H NMR (CDCl$_3$)δ 1.04 (d, J=6.3 Hz, 6H), 2.48 (t, J=4.8 Hz, 2H), 2.51 (t, J=4.8 Hz, 2H), 2.74 (sept, J=6.3 Hz, 1H), 3.37 (t, J=4.8 Hz,2H), 3.55 (t, J=4.8 Hz, 2H), 8.01 (brs, 1H)

1-Isopropylpiperazine

To a solution of 0.29 g of 1-formyl-4-isopropylpiperazine in 10 ml of methanol were added 0.5 ml of hydrochloric acid and 1 ml of water and the mixture was heated under reflux for 2 hours. The reaction solution was distilled off under reduced pressure, a iN aqueous solution of sodium hydroxide was added and the mixture was extracted with chloroform and dried over anhydrous magnesium sulfate. The solvent was distilled off under reduced pressure to afford 0.1 g of the title compound.

Pharmacological test results of the pyridinecarboxamide derivatives (1) of the present invention will be shown below.

For comparison, the compound of Example 10 and the compound of Example 2 of JP-A-5–32630 were used, namely, N-(ll-nitroxy-1-undecanyl)-6-(4-methyl-1-piperazinyl)-nicotinamide (hereinafter referred to as "Comparative Compound 1"), and N-(12-nitroxy-1-dodecanyl)-6-(4-methyl-1-piperazinyl)nicotinamide (hereinafter referred to as "Comparative Compound 2").

The compounds of the present invention will be shown below in terms of the corresponding Example numbers. As an example, "Compound 1" is meant to indicate the compound obtained by the present Example 1.

1. Behavior Suppressing Action

General behavior of mice caused by the pyridinecarboxamide derivatives (I) of the present invention was studied.

Using ddy-strain mice of 7 weeks old, test substance was administered at 100 μl/10 sec to the tail vein and behavior of the animal was observed for one hour. After the administration, sedative animal was evaluated as sedated, while animal with behavioral suppression was evaluated as suppressed.

TABLE 1

|  | R | n | Behavioral suppression (10 mg/kg) |
|---|---|---|---|
| Compound 1 | Et | 12 | Not shown |
| Compound 2 | i-Pr | 12 | Not shown |
| Comparative Compound 1 | Me | 11 | Sedative action |

Behavioral suppression was not observed with Compound 1 and Compound 2. However, it has become apparent that Comparative Compound 1 showed the behavioral suppression and therefore is not desirable as a therapeutic agent for cerebrovascular disorders.

2. Cerebral Protective Action

Cerebral protective action of the pyridinecarboxamide derivatives of this invention were studied (an anti-anoxia action) using a hypoxic model of mice.

Using ddY-strain male mice of 6 weeks old, the test substance of Compound 1 or Compound 2 was intravenously administered to the tail vein at the dose of 1.0 mg/kg. After 30 minutes from the administration, animal were decapitated to measure a gasping duration. This measurement was made by two persons who had not been informed of the test substances and the measured values were averaged to obtain the data. Also, Comparative Compound 1 was administered in the same manner as described above.

It is believed that gasping after decapitation is controlled by the respiratory center and, if the nerve functions are maintained by the respiratory center, the gasping duration would be prolonged. Moreover, it is suggested that the ischemia with decapitation is related to the decrease in the intracerebral glucose which is believed to be essential as a nutrition component in the brain. In view of the foregoing, the pyridinecarboxamide derivatives of this invention can prolong the gasping duration and then are useful as a cerebral protective agent.

The action of each substance will be shown in Table 2, with the gasping duration of Comparative Compound 1 being defined as 1.

TABLE 2

|  | R | n | Gasping duration |
|---|---|---|---|
| Compound 1 | Et | 12 | 1.4 |
| Compound 2 | i-Pr | 12 | 1.5 |
| Comparative Compound 1 | Me | 11 | 1 |

The Compound 1 and Compound 2 had 1.4 and 1.5 times higher cerebral protective action than Comparative Compound 1, respectively. 3. Inhibiting Action on Calcium-Influx From SD-strain male rats, the brain was excised under light ether anesthesia. The hippocampus slice with a thickness of 400 mm was prepared by means of a microslicer and stored in artificial cerebrospinal fluid. The slice was immersed in fura-2/Am 10 mM for one hour to load the pigment. The fluorescent images obtained with the excited wavelengths of 380 nm and 340 nm were taken and analyzed by means of Argus-50 System. The ischemic state was produced by perfusing a solution containing no glucose and saturated with a N$_2$/CO$_2$ gas from 3 minutes to 10 minutes after initiation of the measurement. The drug was dissolved in a perfusion solution and applied from 20 minutes prior to the ischemia to 10 minutes after the ischemia.

The ratios of the data obtained at 340 nm/380 nm were calculated and an average from 2 minutes through 16 minutes after completion of the ischemia was determined.

The perfusate containing no drug was used and similar experiment was performed to prepare a control. The change rates are as shown below in terms of the control value being defined as 100%.

| Compound 1 | 95.2% |
|---|---|
| Comparative Compound 2 | 105.6% |

Compound 1 controlled the Ca-influx in cerebral neuronal cells. No considerably great difference in the change rates was observed between the group given Compound 1 and the group given Comparative Compound 2, but Compound 1 showed an earlier reversion to the baseline during the recovery stage (approximately 10 minutes after the ischemia).

4. Anti-cerebral Edema Action (Obstructive Cerebral Ischemia Model Using Polyvinyl Acetate)

Inhibiting action on cerebral ischemia was studied in an obstructive cerebral ischemia model using polyvinyl acetate.

The obstructive model was prepared as described below. (Hiroyoshi Nishi et al., Stroke 1989, 20:1236–1240)

Wistar-strain male rats weighing 200–350 g were used and fixed at the dorsal position under anesthesia of ether and then the left common carotid artery, internal carotid artery, external carotid artery were isolated. The external carotid artery was ligated, the pterygopalatine artery was fastened with clamp and a cannula was inserted from the external carotid artery toward the branch between the internal carotid artery and the common carotid artery. 5 µl of a 3% polyvinyl acetate/52% ethanol solution in water was injected. After 30 seconds, the clamp was removed from the artery and then the wound sutured. After 24 hours, animal was decapitated and the cerebrum was separated, within 120 seconds from which wet weights of the left cerebrum and the right cerebrum were measured. The left and right cerebra were dried in an oven at 105° C. for 24 hours and then the dry weights were measured. A cerebral water content was calculated according to the following equation:

Cerebral water content (%) = (Wet weight – Dry weight)/Wet weight × 100

Compound 1, Compound 2 or Comparative Compound 2 was intravenously injected to the tail vein at the doses of 1.0 mg/kg and 3.0 mg/kg before 5 minutes from the administration of polyvinyl acetate.

Inhibitory rates of cerebral edema in the cerebral edema model using polyvinyl acetate are shown in Table 3.

TABLE 3

| | R | n | 1 mg/kg | 3 mg/kg |
|---|---|---|---|---|
| Compound 1 | Et | 12 | 29.0% | 61.9% |
| Compound 2 | i-Pr | 12 | 59.1% | |
| Comparative Compound 2 | Me | 12 | 21.5% | 11.3% |

Compounds 1 and 2 inhibited cerebral edema by around 60%, whereas Comparative Compound 2 inhibited only by around 20%.

5. Anti-Cerebral Edema Action (Ischemic Reperfusion Model Using SHR-SP)

The inhibitory action on cerebral edema of the pyridinecarboxamide derivatives of this invention were studied using the SHR-SP models (Spontaneous hypertensive rats which are vulnerable to cerebral hemorrhage).

Male SHR-SP of 15–17 weeks old were measured for the blood pressure one day prior to the test and classified into groups. Both common carotid arteries were separated under pentobarbital anesthesia at 35 mg/kg and common carotid arteries were fastened by clamp to cause ischemia. After 2 hours, clamp was removed from the arteries to reperfuse. After a further 2 hours, the animal was decapitated and cerebrum was excised under ether anesthesia. The cerebrum was dried in an overn at 105° C. for 24 hours and the cerebral water content (%) was calculated.

Cerebral water content (%) = (Wet weight – Dry weight)/Wet weight × 100

Compound 1, Compound 2 and Comparative Compound 2 were intravenously administered twice, that is, immediately after the ischemia and immediately before the reperfusion, at the dose of 1 mg/kg, respectively.

Inhibitory rates of cerebral ischemia by Compound 1, Compound 2 and Comparative Compound 2 are shown in Table 3-2.

TABLE 3-2

| | R | n | |
|---|---|---|---|
| Compound 1 | Et | 12 | 63% |
| Compound 2 | i-Pr | 12 | 71% |
| Comparative Compound 2 | Me | 12 | −90% |

Compound 1 and Compound 2 showed a potent anti-cerebral edema activity, whereas Comparative Compound 2 made cerebral edema worse.

6. Inhibitory Rate of Delayed Neuronal Death

MON/Jms/Gbs-strain male jirds (weighing 60–80 g) were fixed at the dorsal position under 1.5–2.0% halothane anesthesia and the common carotid artery was isolated. Ischemia was caused by fastening the common carotid artery with clamp for 3 minutes and then reperfused. After 7 days, the brain was excised under ether anesthesia and fixed with 10% formalin for 2 days and then tissue slices of the hippocampus were prepared. The hippocampus CA1 cells were stained using HE staining and the survival rate of the CA1 cells was evaluated.

Compound 1 was administered to the carotid artery at the dose of 0.5 mg/kg immediately after the ischemia. Using as a control the case wherein the drug was not administered, inhibitory rate was calculated according to the following equation:

Inhibitory rate =

(1 − (Survival rate of Compound 1 administered $CA1$ cells/Survival rate of control $CA1$ cells) × 100(%)

TABLE 4

| | R | n | Inhibitory rate |
|---|---|---|---|
| Compound 1 | Et | 12 | 20% |

7. Inhibitory Action on Lipid Peroxidation

Inhibitory action on lipid peroxidation was studied using rat brain homogenate.

Wistar-strain male rats (weighing 230–300 g) were decapitated and the cerebrum was quickly excised. A 4 times volume of a solution of 50 mM phosphoric acid and 0.142 mM NaCl (pH 7.4) was added and the mixture was homogenized and then centrifuged at 3000 rpm for 10 minutes. The supernatant thus obtained was prepared so as to give a protein level of 2 mg/ml.

Determination of lipid peroxide was carried out using TBA method (thiobarbituric acid). To the brain homogenate was added Compound 2 so as to give a final concentration of $10^{-4}$M, thereby initiating the reaction. After incubation at 37° C. for 15 minutes, the reaction was stopped in ice by adding a 35% perchloric acid solution. The reaction mixture was centrifuged at 4° C. and 1000 rpm for 5 minutes and to the supernatant thus obtained was added a 0.5% TBA solution. The mixture was boiled at 100° C. for 15 minutes. After cooling, absorbance was determined at 532 nm. 1,1, 3,3-Tetraethoxypropane as a standard was subjected to the reaction in the same manner as above and an amount of lipid peroxide, that is, an amount of the malondialdehyde (MDA) produced was determined from the absorbances.

Inhibitory rate of lipid peroxidation was calculated according to the following equation:

| | R | n | Inhibitory rate of lipid peroxidation (%) |
|---|---|---|---|
| Compound 2 | i-Pr | 12 | 71 |

Inhibitory rate of lipid peroxidation = [1 − {MDA nmol (Compound 2; incubated for 15 min.) − MDA nmol (Compound 2; incubated for 0 min.)}/{MDA nmol (solvent; incubated for 15 min.) − MDA nmol (solvent; incubated for 0 min.)}] × 100(%)

Table 5 demonstrates that the pyridinecarboxamide derivatives of this invention have an inhibitory action on lipid peroxidation.

We claim:

1. A pyridinecarboxamide derivative of the formula (1)

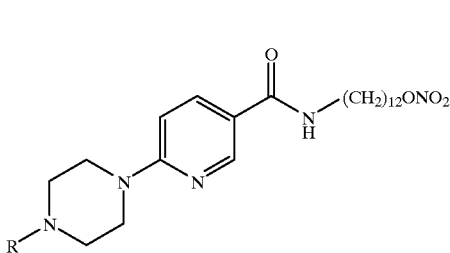

(1)

(wherein R represents an ethyl group or an isopropyl group) or a physiologically acceptable salt thereof.

2. A compound of the formula (2)

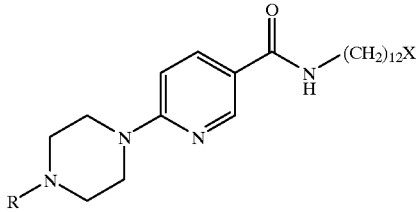

(2)

(wherein R represents an ethyl group or an isopropyl group and X represents a mesyloxy group, a tosyloxy group, a bromine atom or an iodine atom).

3. A process for the preparation of a pyridinecarboxamide derivative represented by the formula (1)

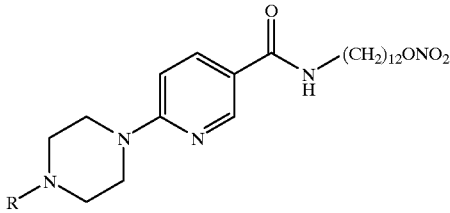

(1)

wherein R represents an ethyl group or an isopropyl group, which comprises reacting a compound represented by the said formula (2)

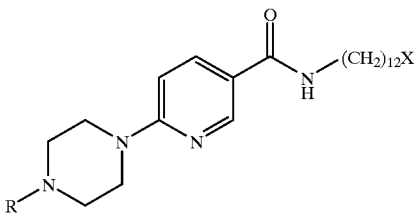

(2)

wherein R represents an ethyl group or an isopropyl group and X represents a hydroxyl group, a mesyloxy group, a tosyloxy group, a bromine atom or an iodine atom, with a nitrating agent.

4. A process for the preparation of a pyridinecarboxamide derivative represented by the formula (1)

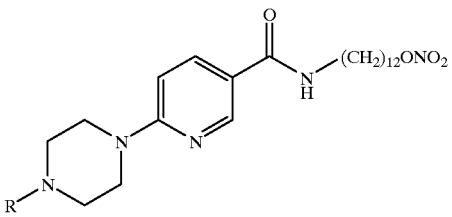

(1)

wherein R represents an ethyl group or an isopropyl group, which comprises reacting an alkali metal salt, halide or acid anhydride of a 6-piperazinylpyridine-3-carboxylic acid of the formula (3)

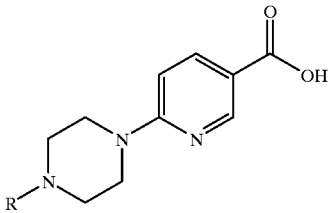

(3)

wherein R represents an ethyl group or an isopropyl group, with 1 2-aminododecyl nitrate represented by the formula (4) or an acid addition salt thereof.

5. A method for treatment of cerebral edema which comprises administering to patients suffering from cerebral edema an effective amount of a pyridinecarboxamide derivative of the formula (1)

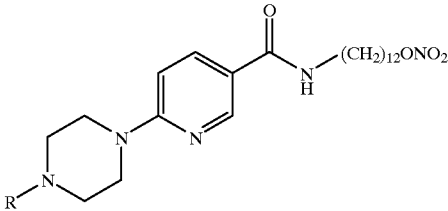

(1)

wherein R represents an ethyl group or an isopropyl group, or a physiologically acceptable salt thereof.

* * * * *

UNITED STATES PATENT AND TRADEMARK OFFICE
CERTIFICATE OF CORRECTION

PATENT NO. : 6,046,201
DATED : April 4, 2000
INVENTOR(S) : Norio Oshida et al.

It is certified that error appears in the above-identified patent and that said Letters Patent is hereby corrected as shown below:

Title page,
Item [75], the Inventor's information; and at the top of Column 1, first paragraph the PCT information is listed incorrectly.

Item [75] should read as follows:
-- [75] Inventors: Norio Oshida; Yoji Mimaki; Hiroaki Satoh, all of Iruma-gun; Shinji Yokoyama, Komoro-shi; Yukiko Muraki; Kazumi Nishimura; Tamiko Hamada; Einosuke Sakurai; Hiroshi Sakai; Toshiji Sugai; Tomomi Tonoike; Koichi Itoh, all of Iruma-gun; all of Japan --.

Column 1,
The first paragraph, should read as follows:
-- This application is a 371 of PCT/JP97/04208, filed Nov. 19, 1997. --

Signed and Sealed this

Twenty-first Day of August, 2001

*Attest:*

*Attesting Officer*

NICHOLAS P. GODICI
*Acting Director of the United States Patent and Trademark Office*